(12) United States Patent
Kheradvar et al.

(10) Patent No.: US 8,702,788 B2
(45) Date of Patent: Apr. 22, 2014

(54) EXPANDABLE STENT THAT COLLAPSES INTO A NON-CONVEX SHAPE AND EXPANDS INTO AN EXPANDED, CONVEX SHAPE

(75) Inventors: Arash Kheradvar, Irvine, CA (US); Morteza Gharib, Altadena, CA (US)

(73) Assignee: California Institute of Technology, Pasadena, CA (US)

( * ) Notice: Subject to any disclaimer, the term of this patent is extended or adjusted under 35 U.S.C. 154(b) by 205 days.

(21) Appl. No.: 13/082,191

(22) Filed: Apr. 7, 2011

(65) Prior Publication Data

US 2011/0251670 A1    Oct. 13, 2011

Related U.S. Application Data

(60) Provisional application No. 61/321,834, filed on Apr. 7, 2010.

(51) Int. Cl.
*A61F 2/82* (2013.01)
(52) U.S. Cl.
USPC .......................................... 623/1.15
(58) Field of Classification Search
USPC ............................... 623/1.15–1.35
See application file for complete search history.

(56) References Cited

U.S. PATENT DOCUMENTS

| | | | |
|---|---|---|---|
| 6,327,772 B1 * | 12/2001 | Zadno-Azizi et al. ......... | 29/557 |
| 6,461,366 B1 | 10/2002 | Seguin | |
| 6,530,952 B2 * | 3/2003 | Vesely ......................... | 623/2.18 |
| 6,582,462 B1 | 6/2003 | Andersen et al. | |
| 6,997,945 B2 * | 2/2006 | St. Germain ................ | 623/1.15 |
| 7,175,656 B2 | 2/2007 | Khairkhahan | |
| 7,628,802 B2 * | 12/2009 | White et al. ................. | 623/1.15 |
| 7,670,365 B2 * | 3/2010 | Gundale et al. ............. | 623/1.11 |
| 7,803,168 B2 | 9/2010 | Gifford et al. | |
| 7,806,921 B2 * | 10/2010 | Hoffman ...................... | 623/1.24 |
| 7,837,727 B2 * | 11/2010 | Goetz et al. ................. | 623/2.18 |
| 7,842,081 B2 * | 11/2010 | Yadin .......................... | 623/1.35 |
| 8,251,067 B2 * | 8/2012 | Hendricksen et al. ... | 128/207.14 |
| 2006/0252624 A1 | 11/2006 | Kuribayashi et al. | |
| 2007/0032857 A1 | 2/2007 | Schmid et al. | |
| 2007/0112418 A1 * | 5/2007 | Eidenschink et al. ....... | 623/1.35 |
| 2008/0154355 A1 | 6/2008 | Benichou et al. | |
| 2008/0255660 A1 | 10/2008 | Guyenot et al. | |
| 2010/0114305 A1 | 5/2010 | Kang et al. | |
| 2010/0152838 A1 | 6/2010 | Kang et al. | |

OTHER PUBLICATIONS

Notification of Transmittal of the International Search Report and the Written Opinion of the International Searching Authority for PCT/US2011/000636.
Notification of Transmittal of the International Preliminary Report on Patentability for PCT/US2011/000636.

* cited by examiner

*Primary Examiner* — Suzette J Gherbi
(74) *Attorney, Agent, or Firm* — Tope-McKay & Associates

(57) ABSTRACT

An expandable stent that can transform between a collapsed state and an expanded state is described. The stent includes a first cross-sectional shape and a second cross-sectional shape. The first cross-sectional shape is a non-convex shape when the stent is in the collapsed state. Alternatively, the second cross-sectional shape is a convex shape when the stent is in an expanded state. The stent can be formed of super elastic Nitinol, which allows it to be shape set in the desired shape. Due to its shape setting properties and the non-convex cross-section, the stent is capable of dramatically reducing its cross-sectional radial profile which is beneficial in a variety of procedures.

18 Claims, 18 Drawing Sheets

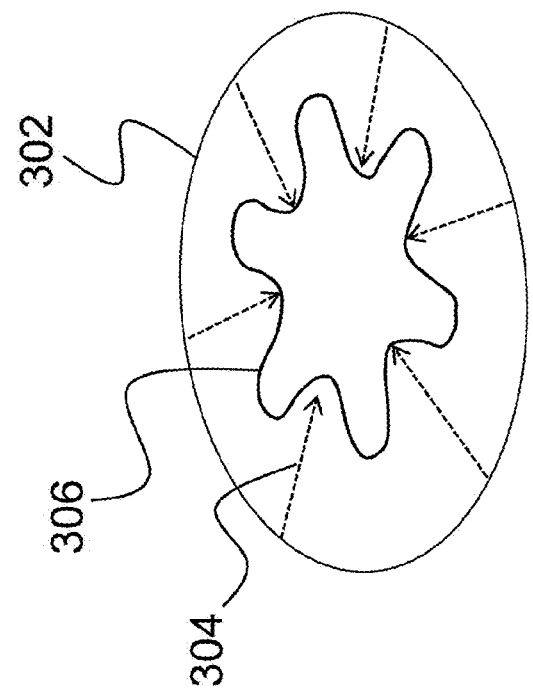
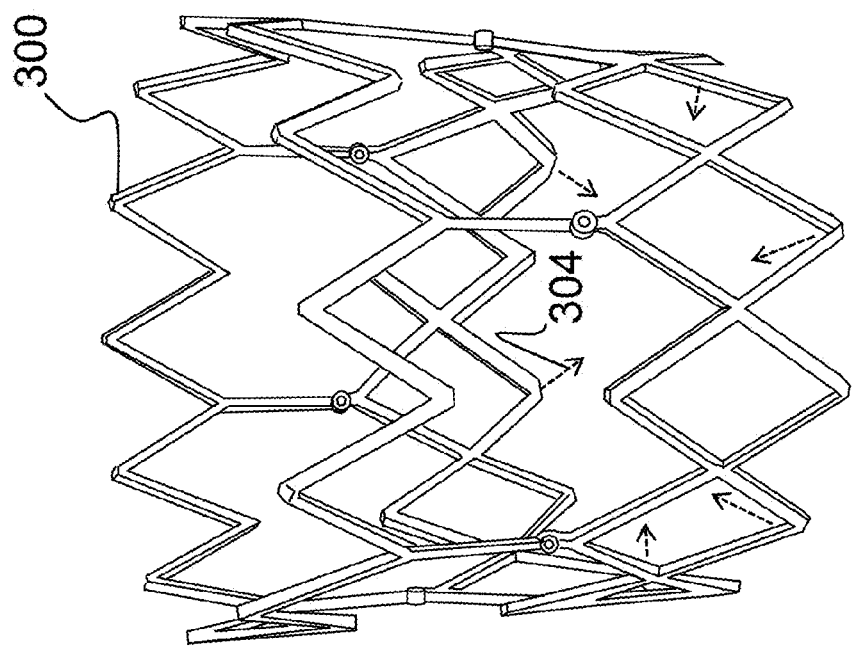
FIG. 3A

EXPANDABLE STENT THAT COLLAPSES INTO A NON-CONVEX SHAPE AND EXPANDS INTO AN EXPANDED, CONVEX SHAPE

PRIORITY CLAIM

The present application is a Non-Provisional Utility patent application of U.S. Provisional Application No. 61/321,834, filed on Apr. 7, 2010, entitled, "Stents that would Collapse into Non-convex structures."

BACKGROUND OF THE INVENTION (1) Field of Invention

The present invention relates to an expandable stent and, more particularly, to an expandable stent that collapses into a non-convex shape and expands into a convex shape.

(2) Description of Related Art

Stents have been devised for a variety of purposes. For example, stents are often formed as coronary stents or used in cardiac valve prostheses for implantation into the human body. Previously, the large diameter and bulky structure of common prosthetic valves required implementation via open heart surgeries. During the past few years, percutaneous heart valve (PHV) replacement and repair has emerged as an additional therapy to potentially avoid the re-operation in young patients with congenital heart disease or severely sick patients. The challenge in PHV technology is to develop a collapsible and durable PHV that can be delivered through a reasonably small diameter lumen catheter, non-interfering with the normal anatomy, and being competent without significant valve stenosis.

For example, a fully formed valve which is deliverable via a catheter is disclosed in U.S. Pat. No. 6,582,462 to Andersen et al. (the '462 patent), the entire contents of which are incorporated herein by reference. The '462 patent discloses a fully formed valve prosthesis comprising a collapsible elastic valve mounted on an elastic stent. The commissural points of the elastic collapsible valve are mounted on the cylindrical surface of the elastic stent. A catheter technique permits delivery of the fully formed valve to the target area without the need for surgical intervention in the body. Once at the target site, the collapsed and fully-formed valve and elastic stent are expanded. A disadvantage to this design is the relatively large size of the compressed radial diameter of the fully formed valve and corresponding stent when delivered to the target area.

Another example is U.S. Pat. No. 6,530,952 to Vesely (the '952 patent), the entire contents of which are incorporated herein by reference. The '952 patent discloses a cardiovascular valve system including a permanent base unit that is affixed to the patient using conventional sutures or staples, and a collapsible valve having a collapsible frame that mates with the permanent base unit, and supports valve leaflets. An installed collapsible frame may be re-collapsed and disengaged from the permanent housing whereas a new collapsible valve is then installed, to resume the function of the prosthesis. As was the case above, a drawback to the device of the '952 patent is that, although collapsed, the valve and corresponding stent have a relatively large, radial diameter.

Another example can be found in U.S. Pat. No. 7,803,168 to Gifford (the '168 patent), the entire contents of which are incorporated herein by reference. The '168 patent teaches a device for decalcifying an aortic valve. The device breaks up calcific deposits in and around the aortic valve through application or removal of heat energy from the calcific deposits. In doing so, the device includes an implantable structure with a balloon. To expand to the structure, the balloon is inflated. Again, the structure includes a relatively large, radial diameter which can create some difficulties in some patients.

The examples provided above illustrate various devices that expand upon arrival at the expansion point within the heart or other desired location. While operable for percutaneous insertion or other uses, the examples require stents having a relatively large, radial diameter.

Another example can be found in U.S. Pat. No. 7,175,656 to Khairkhahan (the '656 patent), the entire contents of which are incorporated herein by reference. The '656 patent teaches a different form of a valve replacement in which additional stent deployment mechanisms are obviated. As described in the '656 patent, the stent mechanism can be formed of a framework of resilient metals, such as superelastic shape memory alloys. Thus, once deployed to the appropriate location, the material of the stent itself causes its expansion into the requisite shape. While the '656 patent teaches use of a superelastic shape memory alloy, it still requires a stent with a relatively large, radial diameter.

Each of the prior art designs has certain disadvantages. However, they all share the common disadvantage in that the stents possess a radial diameter that is undesirable.

Thus, a continuing need exists for a deployable stent which has a minimal radial profile to increase the efficacy of reaching the desired deployment location and minimize the risk to a patient.

SUMMARY OF INVENTION

The present invention relates to an expandable construct (e.g., stent) that can transform between a collapsed state and an expanded state. The stent includes a first cross-sectional shape and a second cross-sectional shape. The first cross-sectional shape is a non-convex shape when the stent is in the collapsed state. Alternatively, the second cross-sectional shape is a convex shape when the stent is in an expanded state. Thus, the stent is expandable from the collapsed state to the expanded state, such that upon expansion, the stent transforms from having the first cross-sectional non-convex shape into the second cross-sectional convex shape.

To form the con-convex shape, the stent is made of a material that allows it to be shape set. For example, the stent can be formed of an elastic material, a super elastic material (e.g., super elastic Nitinol), a shape memory material (e.g., a shape memory alloy such as Nitinol), and a magnetic memory material (e.g., magnetic shape memory alloys, such as $Ni_2MnGa$). In another aspect, the stent can be formed of a dissolving material (e.g., polylactic acid) to allow it to dissolve after being applied for a certain amount of time.

As can be appreciated by one skilled in the art, due to its shape setting properties and the non-convex cross-section, the stent is capable of dramatically reducing its cross-sectional radial profile which is beneficial in a variety of procedures. For example, the stent can be formed as a component of a heart valve. As another example, the stent can be a component of a coronary stent system. In yet another example, the stent is a ureteral stein used to maintain the patency of a ureter. The stent can also be formed as a prostatic stent, or be drug coated to operate as a drug eluting stent. In another example, the stent can be a component of a peripheral artery angioplasty. Further, the stent can be formed as a component of a stent graft used for endovascular surgery. Thus, while the examples provide above enable one skilled in the art to envision various forms and uses of the stent, the present invention is not intended to be limited thereto as the stent can be used in any circumstance where a reduced radial diameter is desirable.

Finally, as can be appreciated by one skilled in the art, the present invention also comprises a method for forming and using the invention described herein. For example, the construct (e.g., stent) can be formed by performing acts of collapsing a stent radially into a stent having a cross-sectional convex shape; applying a load to at least one location on the stent to form a collapsed stent having a cross-sectional non-convex shape; and shape setting the stent to having a shape set cross-sectional non-convex shape. Alternatively, the stent can be applied to a desired location by performing acts of inserting the collapsed stent having a cross-sectional non-convex shape into a user until reaching a desired location; and causing the collapsed stent to transform into an expanded stent having a cross-sectional convex shape.

BRIEF DESCRIPTION OF THE DRAWINGS

The objects, features and advantages of the present invention will be apparent from the following detailed descriptions of the various aspects of the invention in conjunction with reference to the following drawings, where:

FIG. 3A is an illustration of a fully expanded stent and its cross-sectional profile, depicted as contrasted with the reduced cross-sectional profile of the collapsed stent;

FIG. 6I is an illustration of a collapsed stent having a cross-sectional non-convex shape.

DETAILED DESCRIPTION

The present invention relates to an expandable stent and, more particularly, to an expandable stent that collapses into a non-convex shape and expands into a convex shape. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(1) Description

Figure 1:
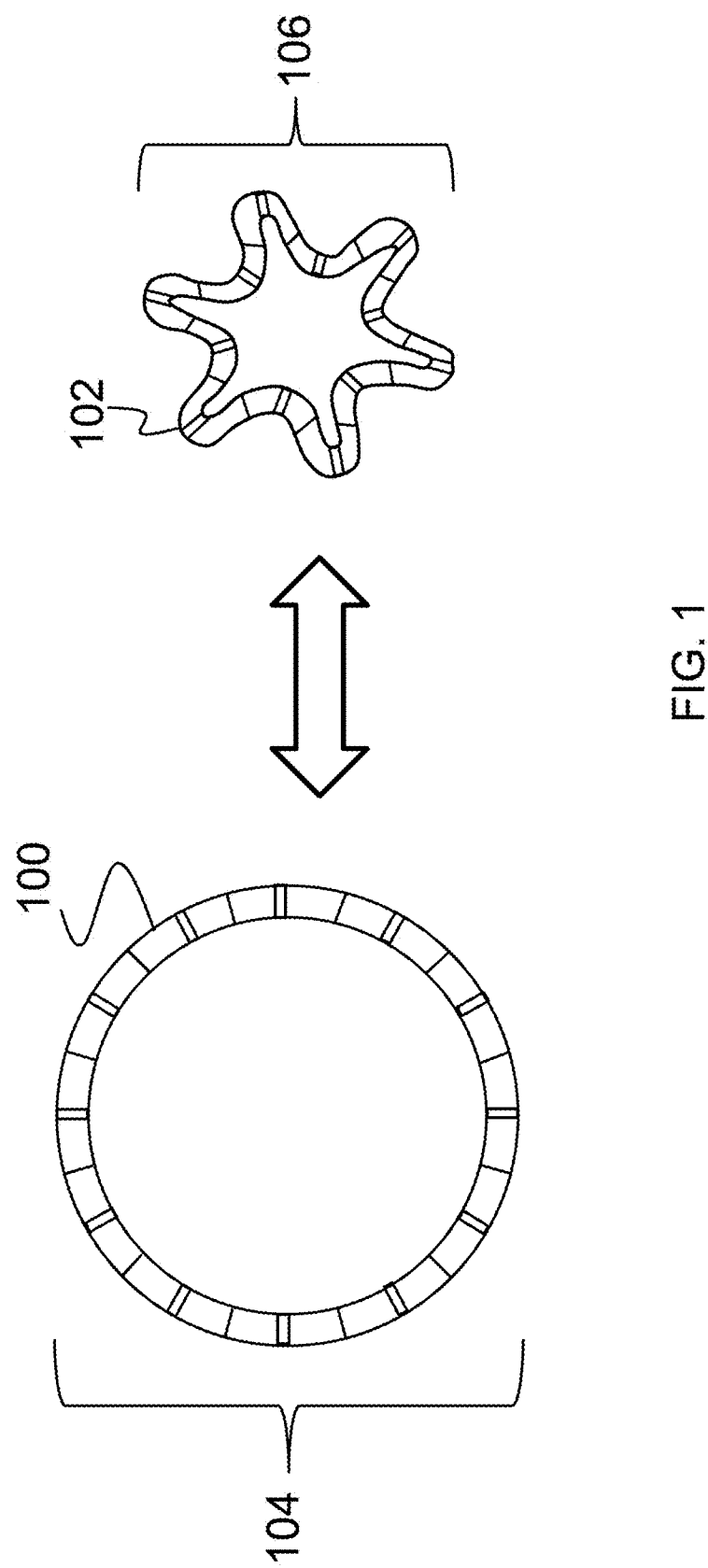
FIG. 1 is a cross-sectional view illustration, depicting the transformation between an expanded stent and a collapsed stent.

As noted above, the present invention is directed to an expandable construct (e.g., stent) that collapses into a non-convex shape and expands into a convex shape. Thus, the present invention is any type of construct that would size down into a collapsed, non-convex structure, a non-limiting example of which includes a stent. As shown in FIG. 1, the present invention is based on transforming the primary convex cross-section of an expanded stent 100 into a non-convex cross section when collapsed 102, thus reducing the overall profile size of a collapsed stent 102 through minimizing the intra-stent space. As a non-limiting example, the expanded stent 100 has an outer diameter 104 of twenty five (25) millimeter (mm), which is to be contrasted with the collapsed stent 102, which has an outer diameter 106 of four (4) mm.

Figure 2:
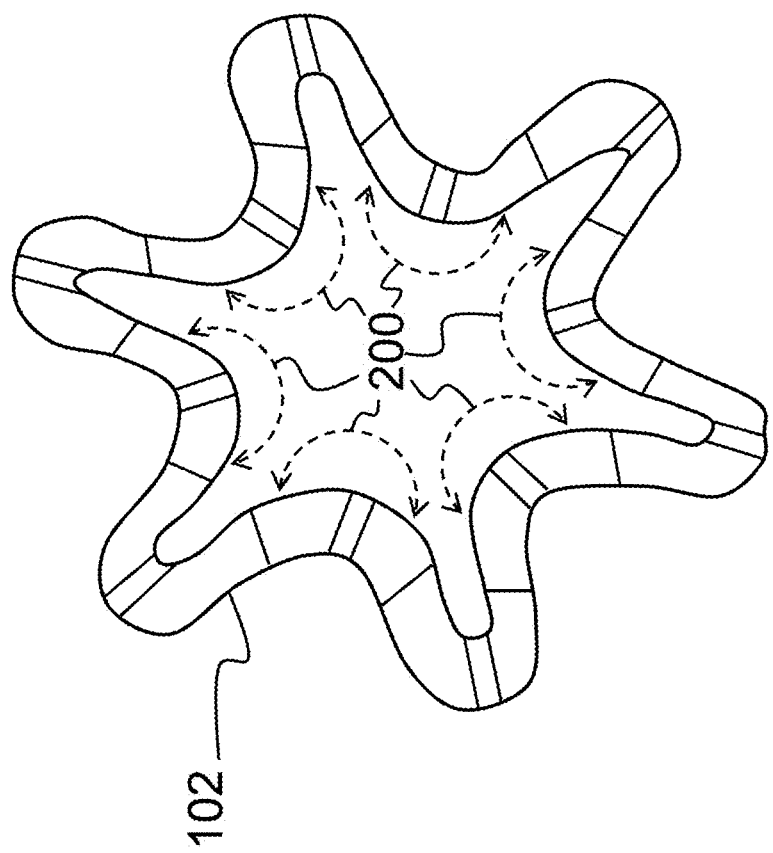
FIG. 2 is a cross-sectional view illustration of a collapsed stent.

A convex cross-section is polygonal shape whose interior is a convex set. A convex polygon is defined as a polygon with all its interior angles less than 180 degrees. Alternatively and as shown in FIG. 2, a polygon that is not convex is called concave or reentrant. FIG. 2 illustrates the collapsed stent 102 as a concave polygon (e.g., non-convex shape). A concave polygon will always have at least one interior angle 200 with a measure that is greater than 180 degrees. As the number of interior angles with a measure that is greater than 180 degrees increases, the overall shape approaches a fractal pattern. As a non-limiting example and as depicted in FIG. 2, the concave polygon can include six (or any suitable number) interior angles 200 that are greater than 180 degrees. This shape transformation would allow for the reduction of effective diameter (occupied cross-section) in its collapsed state while preserving the circumference of the stent in its fully open state stretched state.

This is further illustrated in FIG. 3A, which shows a fully expanded stent 300 and its cross-sectional profile 302. The stent is formed such that upon contraction, portions of the stent 300 move inward 304 to create each of the angles greater than 180 degrees. This results in the collapsed stent, which has a reduced cross-sectional profile 306.

Figure 3B:
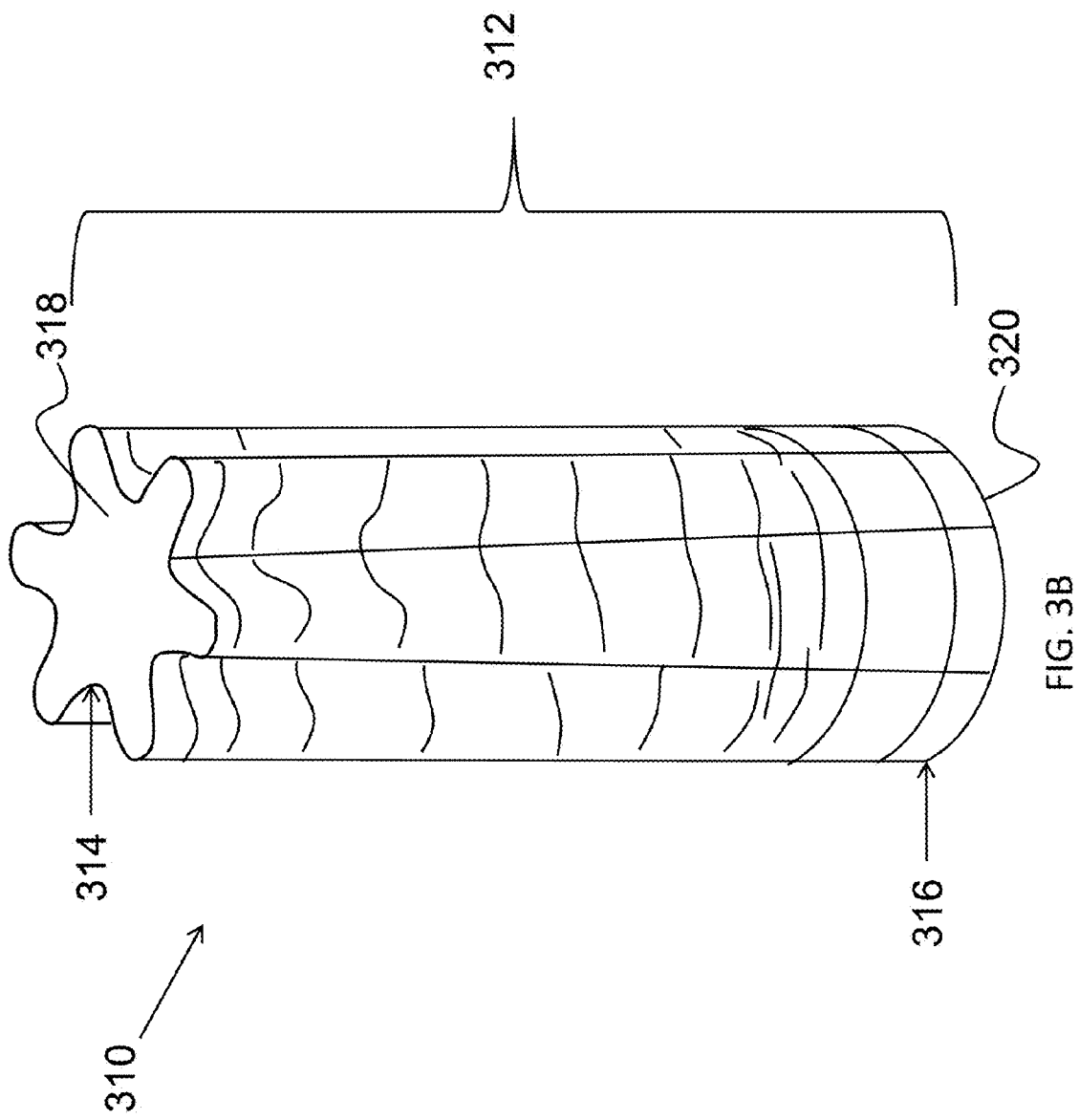
FIG. 3B is an illustration of a collapsed stent in which the cross-sectional cut is not uniform along a length of the stent.

As described herein, it is desirable to have the stent change between a collapsed non-convex shape to a expanded convex shape. However, as can be appreciated by one skilled in the art, the second expanded state does not necessarily have to be convex and, as desired, can be formed such that it also includes a non-convex state. Thus, in one aspect, the stent can transform from a collapsed, first cross-sectional shape that is non-convex into an expanded, second cross-sectional shape that is also non-convex (or partially convex or partially non-convex). In yet another aspect and as depicted in FIG. 3B, the stent 310 can be formed such that the cross-sectional cut is not uniform along the length 312 of the stent. For example, a cross-section at a first point 314 along the stent could be non-convex while another cross-section along the length 312 of the stein 310 at a second point 316 could be convex (or any variation therebetween). Thus, in this example, the cross-section in the collapsed state 310 would vary along the length 312 of the stent 310 from a non-convex shape 318 to a convex shape 320. In other words, the cross-sectional shape of the stent along its length is unequal and non-uniform.

In order to accomplish the transformation from a non-convex shape into a convex shape, the shape can be enforced using hinges, or through special heat treatment when the stent is externally loaded into a non-convex shape. As noted in further detail below, the stent can be formed of a super elastic material (e.g., super elastic Nitinol) that is shape set, which allows the shape of the stent to be set such that it expands from a collapsed non-convex shape into an expanded, convex shape.

Figure 4:
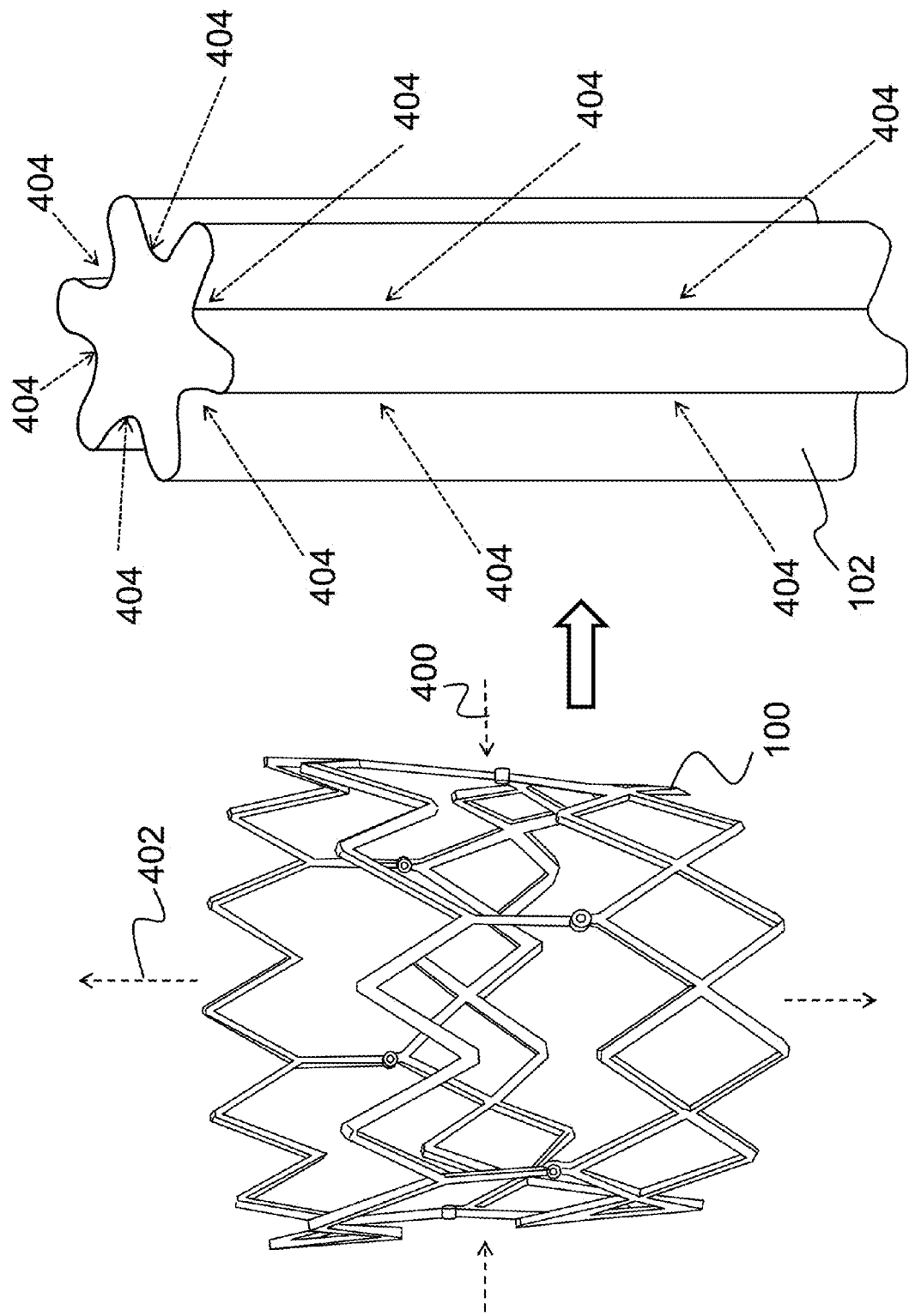
FIG. 4 is an illustration depicting a fully expanded stent and its transformation to a collapsed stent.

For example and as shown in FIG. 4, in order to form the collapsed non-convex shape, the expanded stent 100 is compressed radially 400, which causes lateral expansion 402. Further, a load can be applied to the stent by pushing 404 on some parts of the stent to hold it in the desired non-convex form (i.e., the collapsed stent 102). Once the load is applied to shape the stent into the desired non-convex collapsed stent 102 shape, the collapsed stent is shape set using a shape setting technique that is commonly understood by those skilled in the art. A non-limiting example of a shape setting technique is heat treatment. Because of the properties of the material that the stent is formed of, it can be shape set such that it will transform to or between the non-convex form and the convex form, depending on the desired application.

The stent structure can be made of any suitable material that allows for it to expand from a non-convex or partially convex cross-section when it is fully or partially collapsed into a convex or semi-convex shape cross-section when fully or partially expanded (or vice versa if appropriate). As non-limiting examples, the stent structure can be made of elastic material such as Stainless steel or a superelastic material such as superelastic Nitinol. As another non-limiting example, the stent can be made of a shape memory material such as Nitinol and/or a magnetic memory material. In another aspect, the stent can be formed of a dissolving material to allow it to dissolve after being applied for a certain amount of time, a non-limiting example of such a dissolving material is polylactic acid.

Figures 5A, 5B:
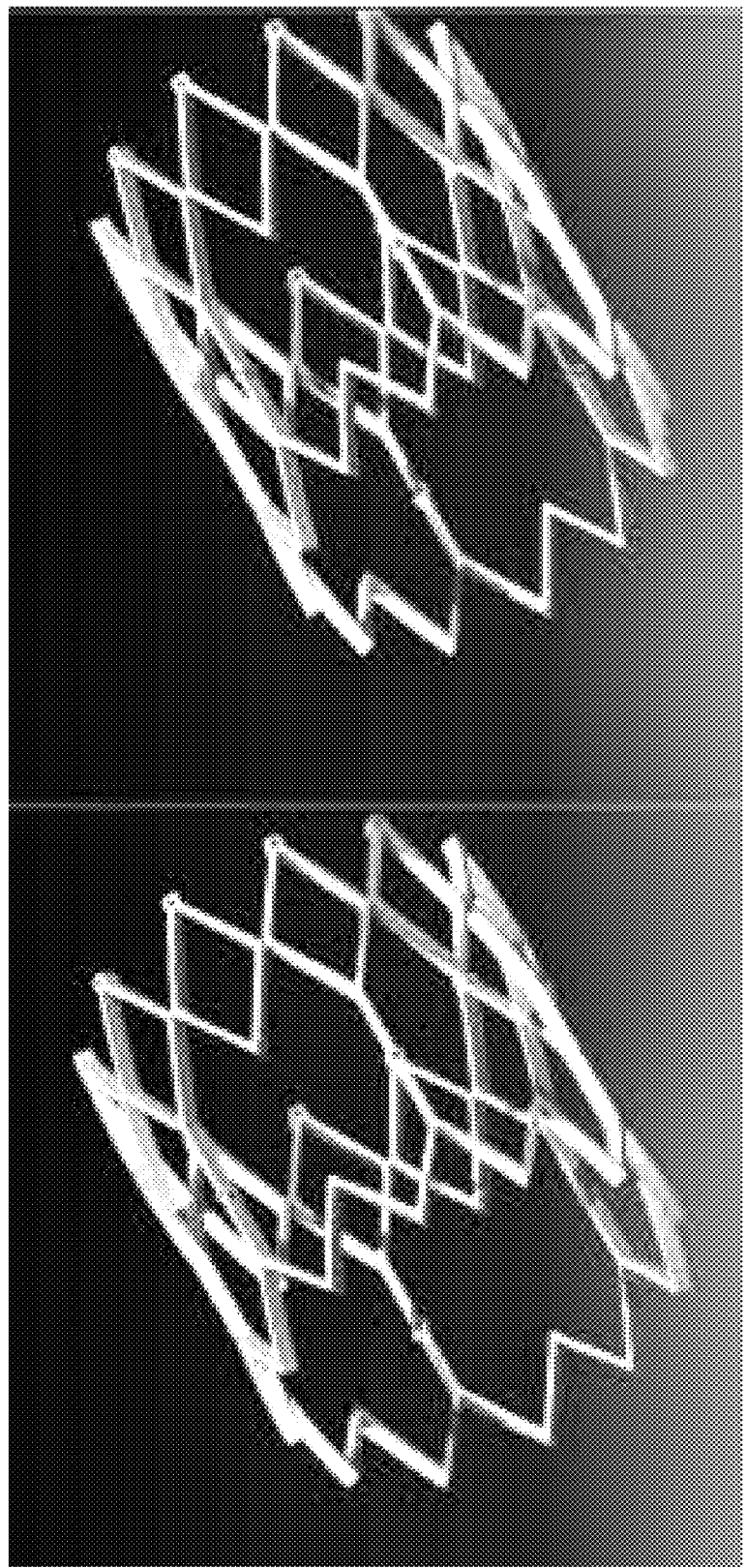
FIG. 5A is an illustration of a fully expanded stent.
FIG. 5B is an illustration of a collapsing stent.
Figures 5C, 5D:
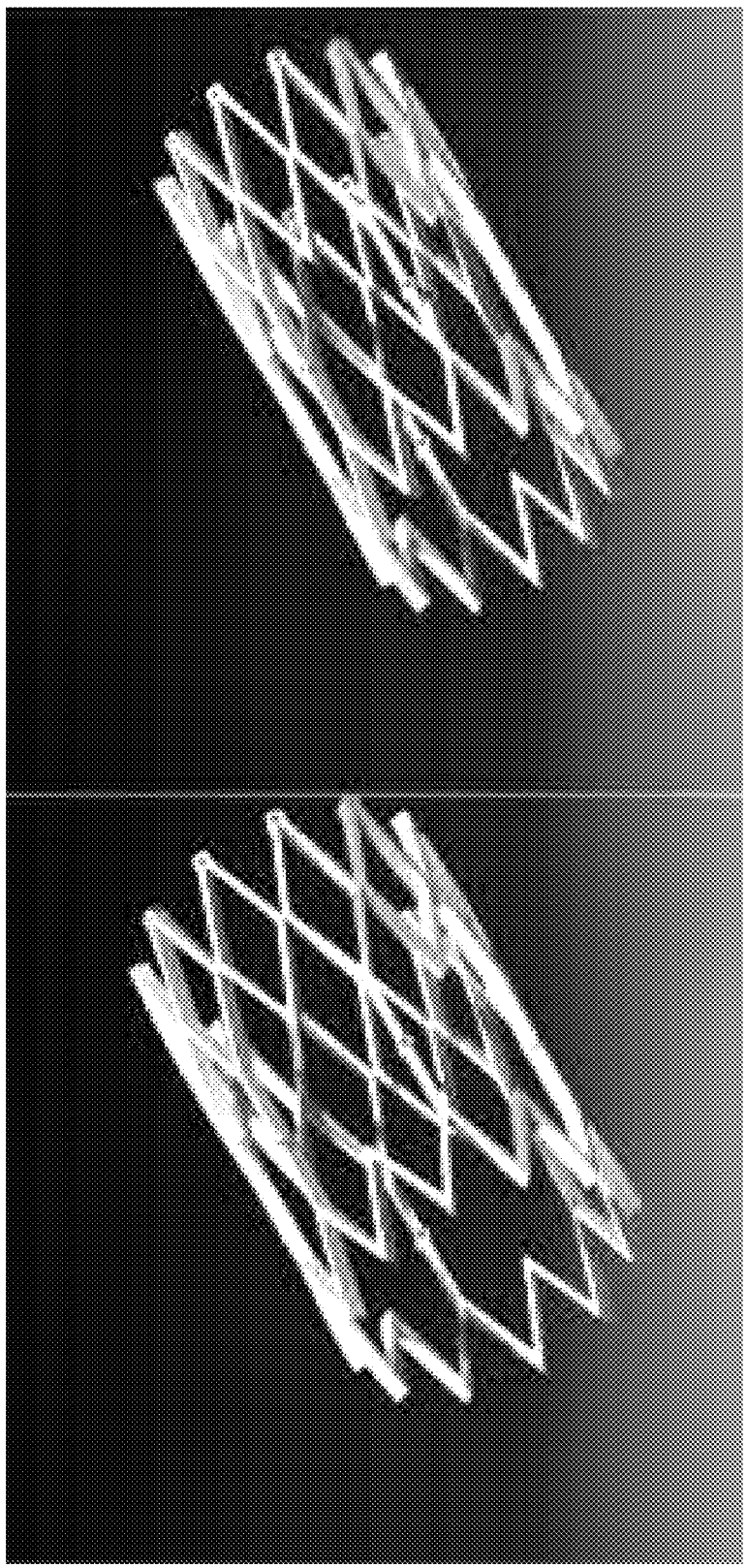
FIG. 5C is an illustration of a collapsing stent.
FIG. 5D is an illustration of a collapsing stent.
Figures 5E, 5F:
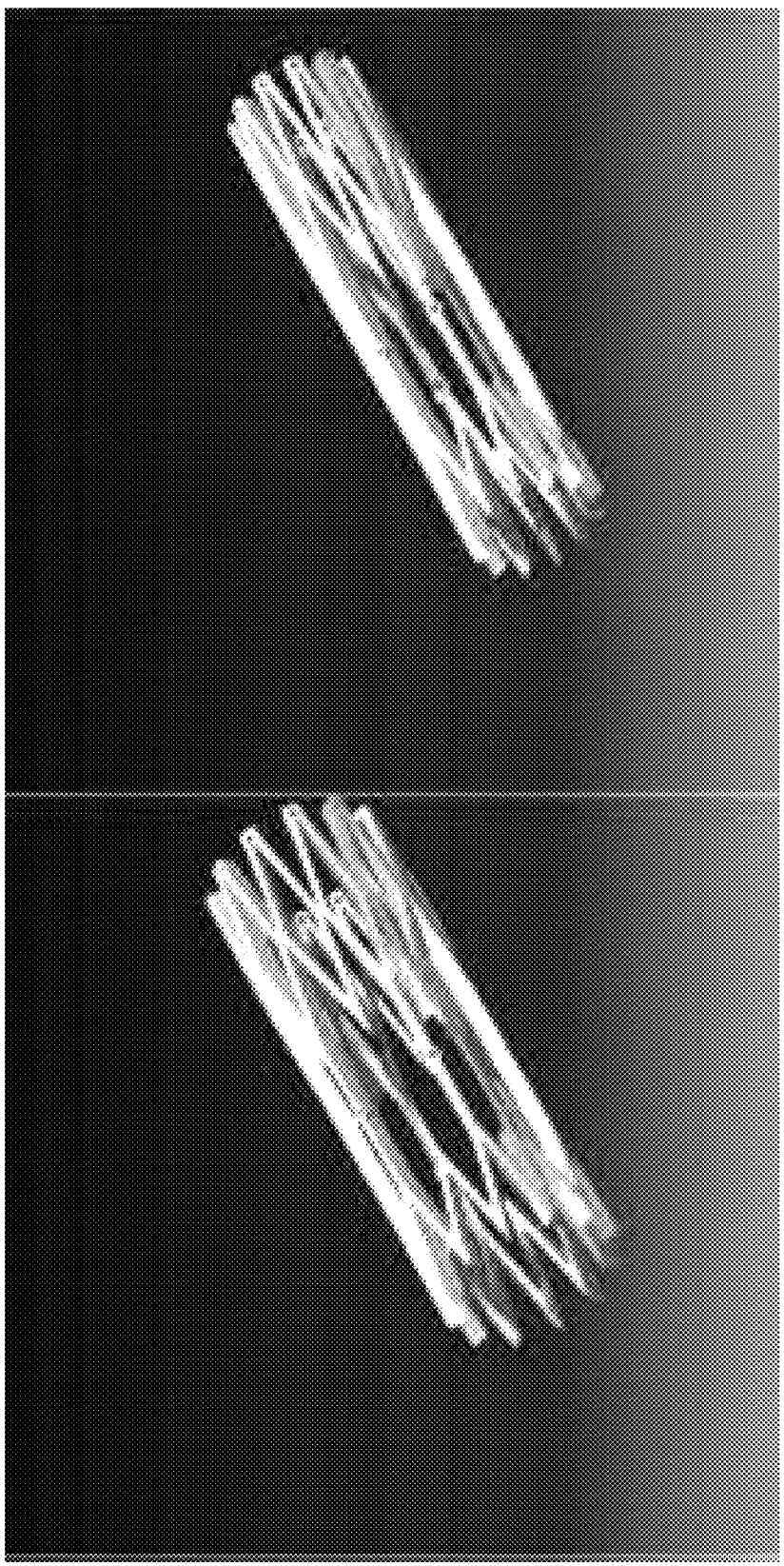
FIG. 5E is an illustration of a collapsing stent.
FIG. 5F is an illustration of a collapsing stent.
Figure 5G:
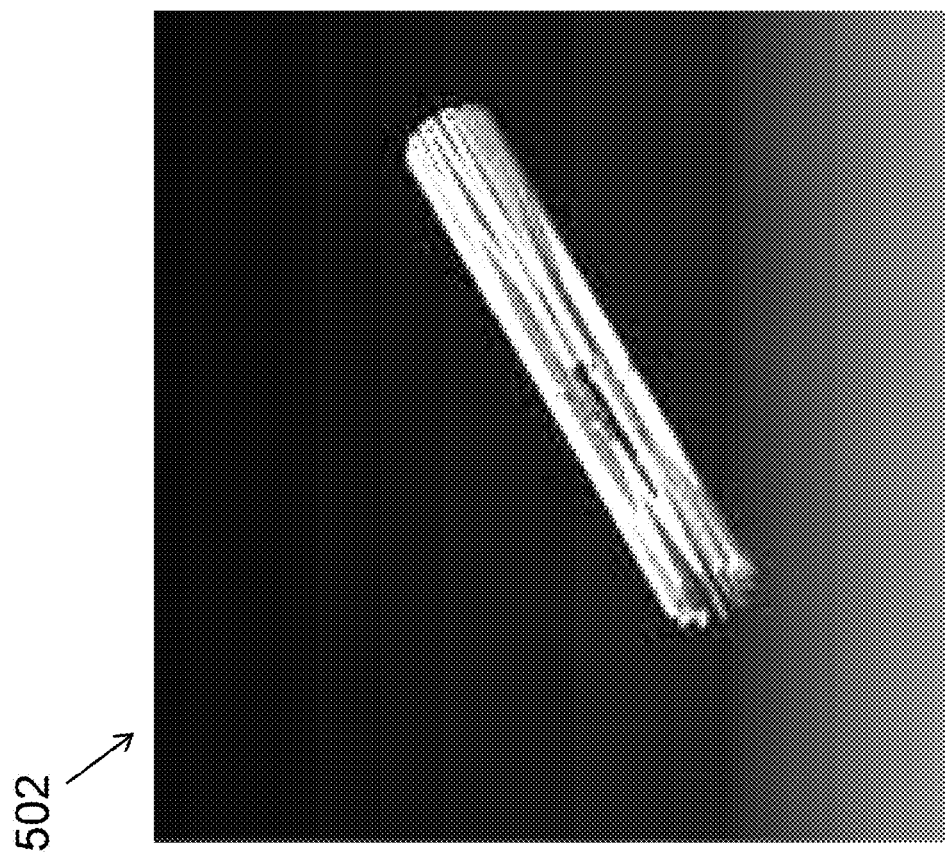
FIG. 5G is an illustration of a collapsed stent.
Figure 6A:
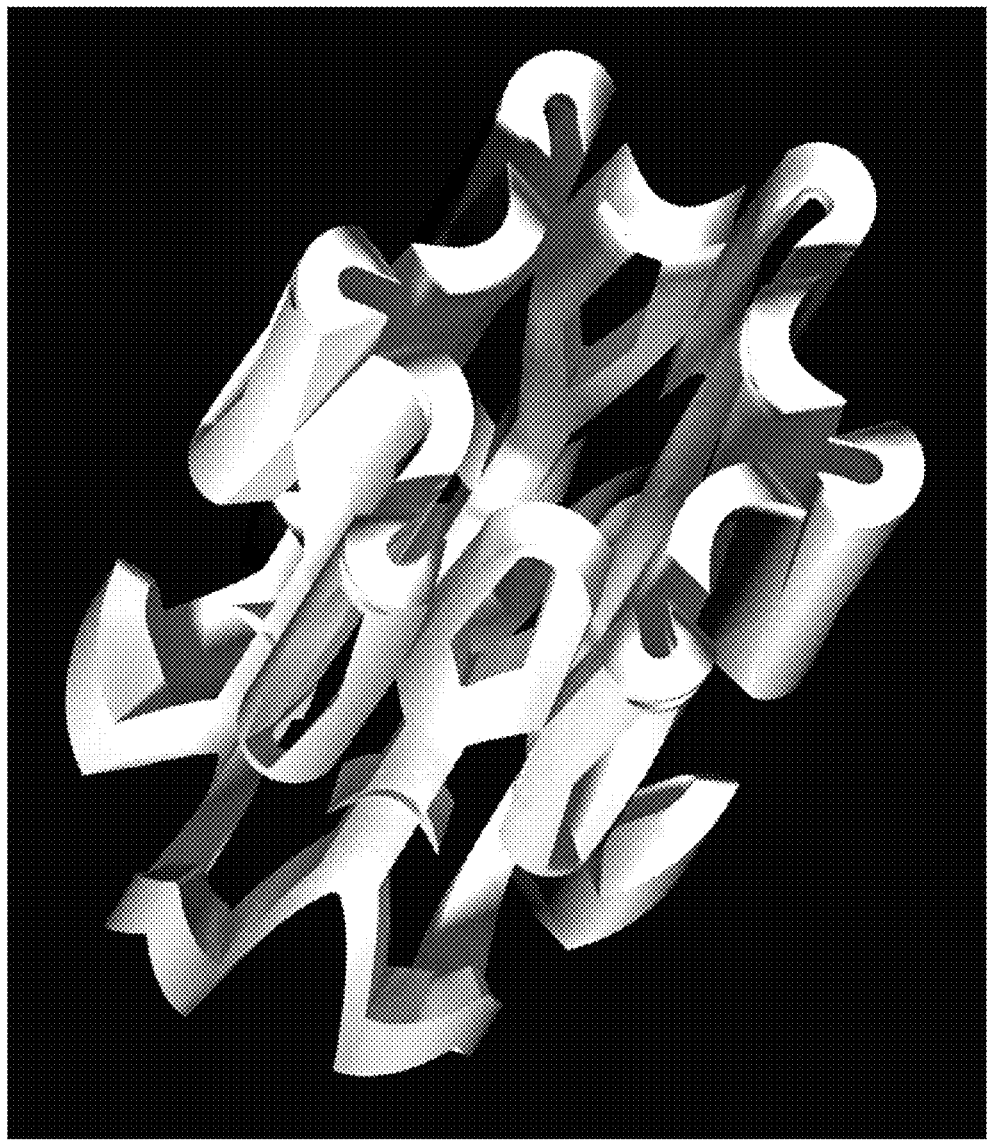
FIG. 6A is an illustration of a collapsed stent having a cross-sectional non-convex shape.
Figure 6B:
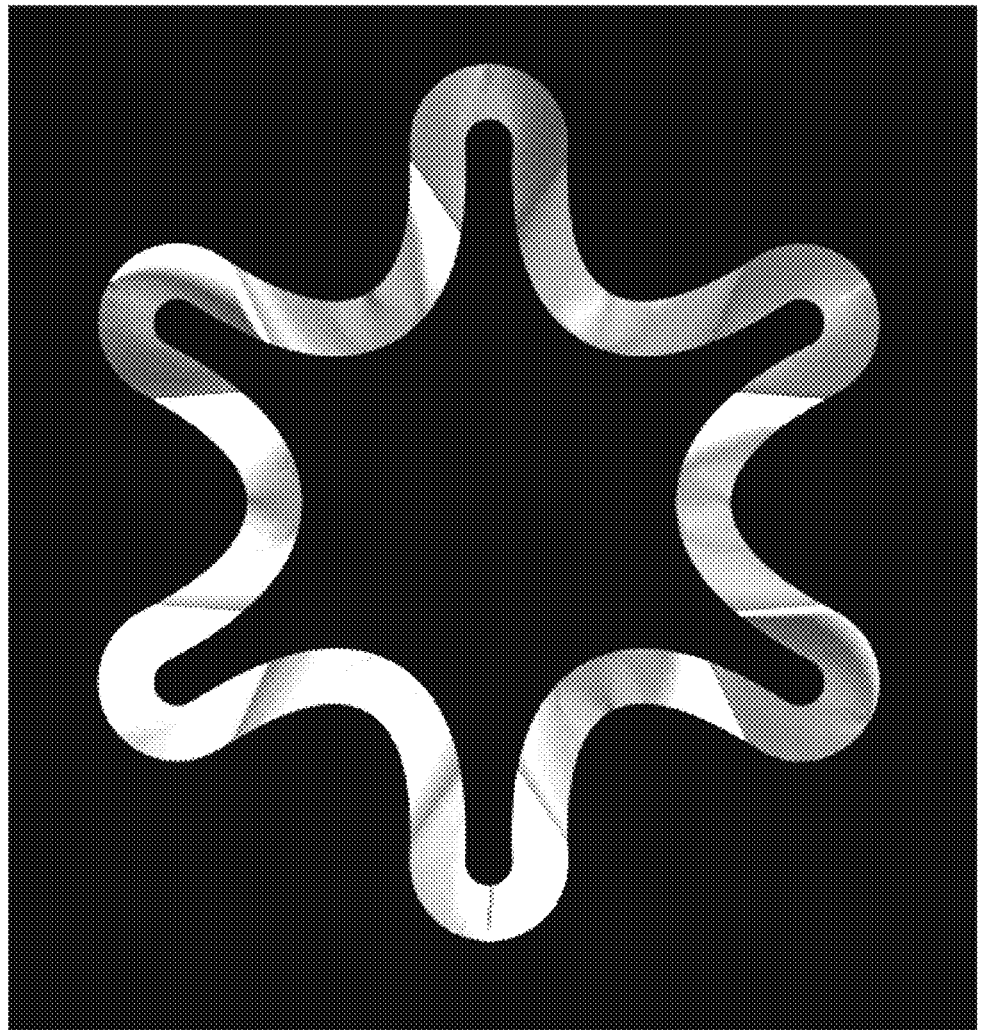
FIG. 6B is an illustration of a collapsed stent having a cross-sectional non-convex shape.
Figure 6C:
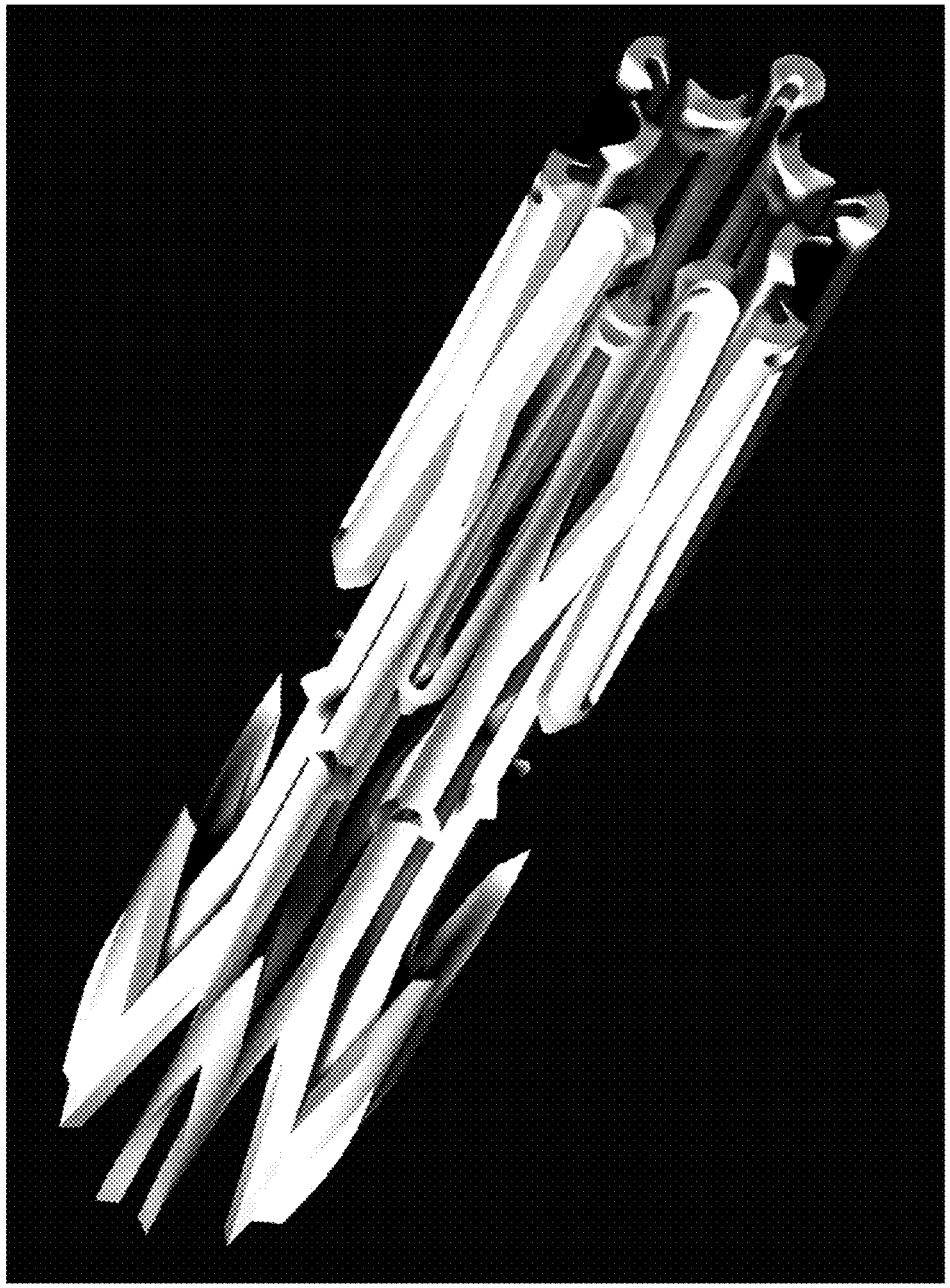
FIG. 6C is an illustration of a collapsed stent having a cross-sectional non-convex shape.
Figure 6D:
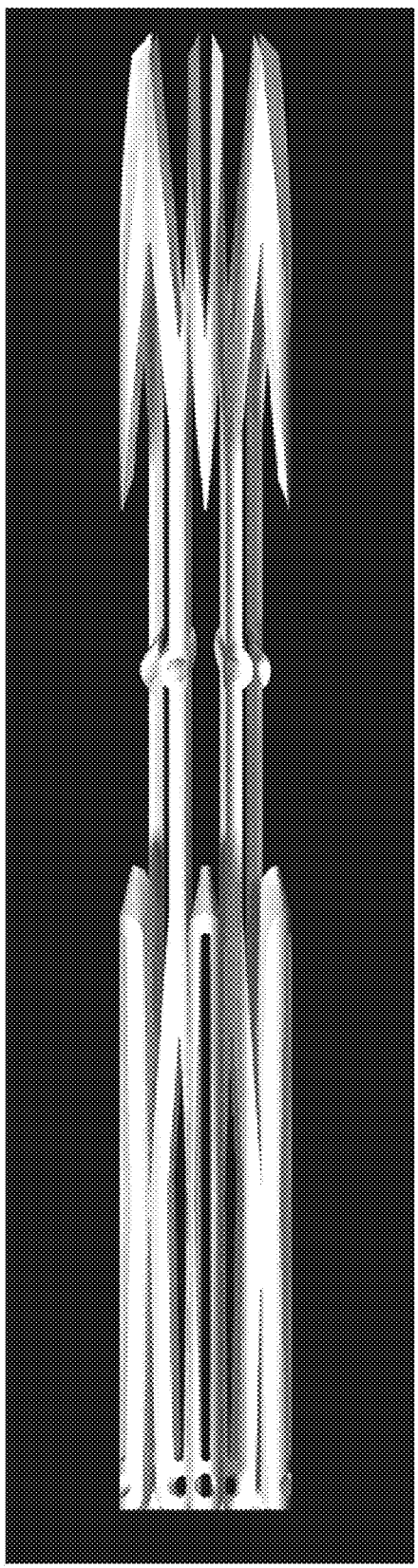
FIG. 6D is an illustration of a collapsed stent having a cross-sectional non-convex shape.
Figure 6E:
FIG. 6E is an illustration of a collapsed stent having a cross-sectional non-convex shape.
Figure 6F:
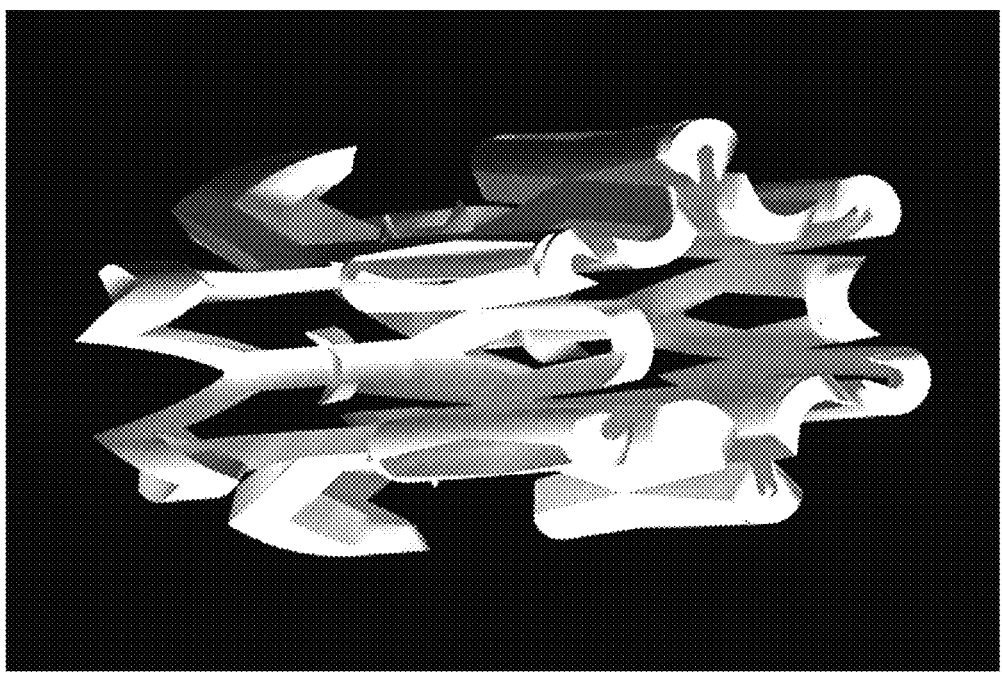
FIG. 6F is an illustration of a collapsed stent having a cross-sectional non-convex shape.
Figure 6G:
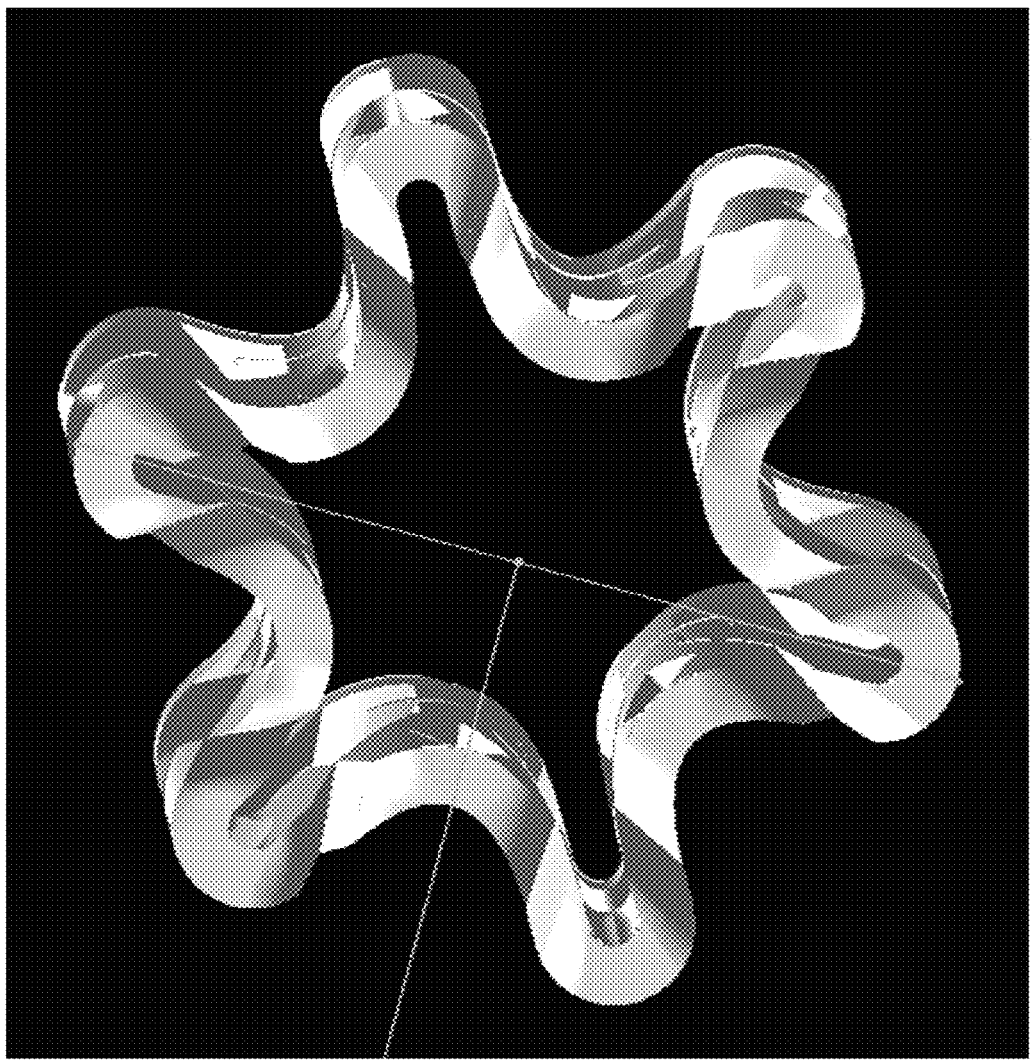
FIG. 6G is an illustration of a collapsed stent having a cross-sectional non-convex shape.
Figure 6H:
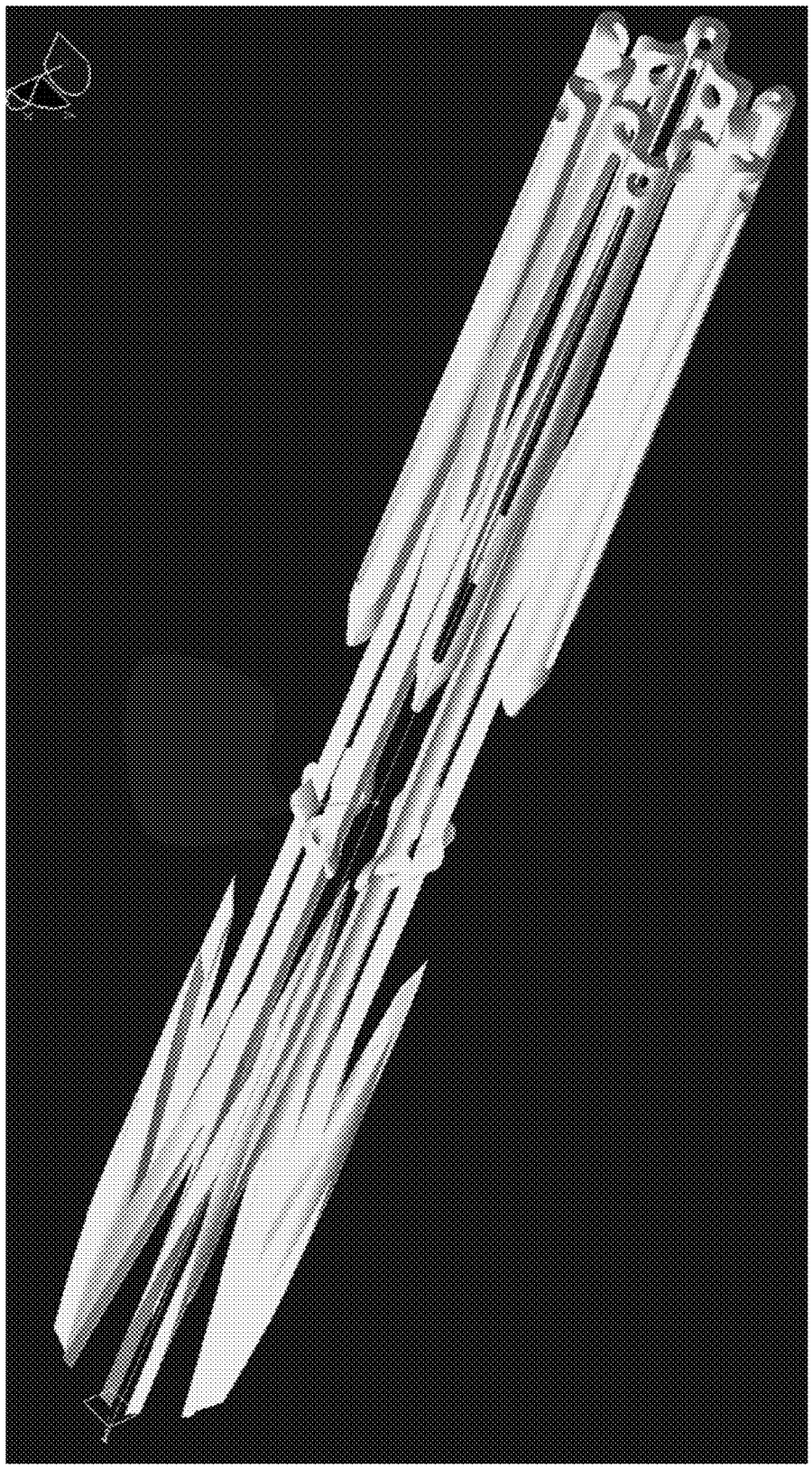
FIG. 6H is an illustration of a collapsed stent having a cross-sectional non-convex shape.
Figure 61:
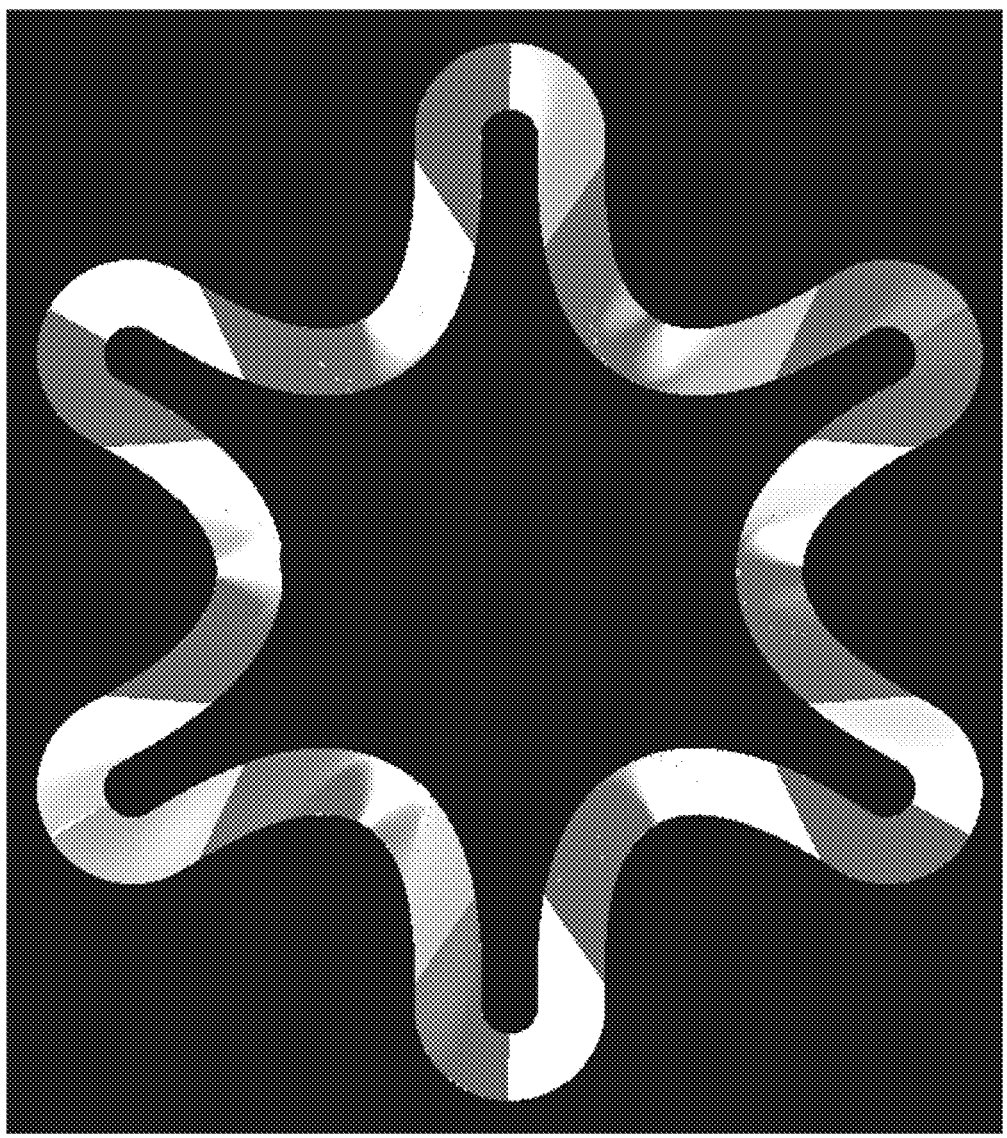

The collapse from the expanded stent 500 into the collapsed stent 502 is further illustrated in FIGS. 5A through 5G. FIG. 5A illustrates a fully expanded stent 500, which is progressively collapsed through FIGS. 5B through 5F. Finally, FIG. 5G shows a radially collapsed stent 502.

Once radially collapsed, a load can be applied to the stent (as depicted in FIG. 4) to form the non-convex shape, which is then shape set using a variety of techniques. FIGS. 6A through 6I depict a collapsed stent 600 having a non-convex cross-sectional shape. The collapsed stent 600 is depicted through FIGS. 6A through 6I from various view-points.

As noted herein, an advantage of the present invention is that once it is collapsed and formed into the non-convex shape, it includes a dramatically reduced radial diameter. Thereafter, once deployed to the desired location, the stent can be activated or otherwise caused to expand to the fully expanded stent form. Such expansion can be performed using a variety of techniques, depending on the material involved and the selected application.

For example, in the case of a temperature dependent shape memory material, the stent can be insulated and applied to the desired location. Thereafter, the insulation can be removed to expose the stent to the target temperature (e.g., body temperature). After heating to the target temperature, which also could be the transformation temperature, the stent will change shape to the desired shape. In one non-limiting example, the stent can be used with a percutaneous heart valve and positioned within the appropriate cavity. After removing the insulation, the stent will quickly heat to body temperature which will cause it to expand and become a fully expanded stent.

Another example can be described through the use of a magnetic shape memory material. In this example, the stent can be applied to a user's body in its collapsed form. Thereafter, the user can be exposed to a certain magnetic field (such as an MRI machine), which would cause the stent to take on its new shape (e.g., expanded, convex shape). As can be appreciated by one skilled in the art, the present invention is not limited directionally from the collapsed state to the expanded state. For example, one skilled in the art can understand that circumstances may arise where it would be desirable to cause the stent to change from the expanded state to the collapsed state (such as when one would want to remove a stent). In the magnetic shape memory example, the stent can be formed such that upon exposure to a certain magnetic field, the stent would collapse, thereby allowing removal of the stent. Alternatively, it may be desirable to insert the stent in the collapsed form while exposed to the magnetic field such that upon removal of the magnetic field, the stent would expand.

As another example and as noted above, a superelastic material can be used. In this example, the collapsed, non-convex stent can be held under a load (e.g., guide wire, catheter, etc.) and applied to the desired location. Thereafter, the load can be released which will return the stent to the expanded, convex shape.

As can be appreciated, a stein that is capable of dramatically reducing its cross-sectional radial profile would be beneficial in a variety of procedures. For example, the stent according to the present invention can be a component of a heart valve, used in a coronary vasculature or is a component of a coronary stent system, formed as a ureteral stent used to maintain the patency of a ureter, used as a prostatic stent or as a component of it, used as a drug eluting stent (that is drug coated), used as a component of a peripheral artery angioplasty, and be a component of a stent graft used for endovascular surgery.

What is claimed is:

1. An expandable construct that can transform between a collapsed state and an expanded state, comprising:
   an expandable construct having a first cross-sectional shape and a second cross-sectional shape, the first cross-sectional shape being a non-convex shape when the expandable construct is in a collapsed state and the second cross-sectional shape being a convex shape when the expandable construct is in an expanded state; and
   wherein the first cross-sectional shape is a non-convex shape that includes at least one interior angle that is greater than 180 degrees.

2. The expandable construct as set forth in claim 1, wherein the construct is a stent, and wherein the construct has an outer diameter in each of the collapsed and expanded states, such that the outer diameter of the expanded state is greater than the outer diameter of the collapsed state.

3. The expandable construct as set forth in claim 1, wherein the construct is a stent that is formed of a dissolving material.

4. The expandable construct as set firth in claim 1, wherein the expandable construct includes a length and has a form such that a cross-sectional shape is unequal along its length.

5. The expandable construct as set forth in claim 1, wherein the construct is a stent and the stent is expandable from the collapsed state to the expanded state, such that upon expansion, the stent transforms from having the first cross-sectional non-convex shape into the second cross-sectional convex shape.

6. The expandable construct as set forth in claim 1, wherein the construct is made of elastic material.

7. The expandable construct as set forth in claim 1, wherein the construct is made of a material selected from a group consisting of a super elastic material, a shape-memory material, and a magnetic memory material.

8. The expandable construct as set forth in claim 1, wherein the construct is made of a material, selected from a group consisting of a super elastic Nitinol and a shape-memory Nitinol.

9. The expandable construct as set forth in claim 1, wherein the construct is a component of a heart valve.

10. The expandable construct as set forth in claim 1, wherein the construct is a component of a Coronary stent system.

11. The expandable construct as set forth in claim 1, wherein the construct is a ureteral stent.

12. The expandable construct as set forth in claim 1, wherein the construct is a prostatic stem.

13. The expandable construct as set forth in claim 1, wherein the construct is drug coated to operate as a drug eluting stem.

14. The expandable construct as set forth in claim 1, wherein the construct is a component of a peripheral artery angioplasty.

15. The expandable construct as set forth in claim 1, wherein construct is a component of a stein graft used for endovascular surgery.

16. A method for forming a construct, comprising acts of:
   collapsing a construct radially to have a cross-sectional convex shape;
   applying a load to at least one location on the construct to form a collapsed construct having a cross-sectional non-convex shape with at least one interior angle that is greater than 180 degrees; and
   shape setting the construct to having a shape set cross-sectional non-convex shape with at least one interior angle that is greater than 180 degrees.

17. The method as set forth in claim 13, wherein in collapsing a construct radially, the construct is a stent.

18. A method for applying a stem to a desired location, comprising acts of:
   inserting a collapsed stent having a cross-sectional non-convex shape with at least one interior angle that is greater than 180 degrees into a user until reaching a desired location; and
   causing the collapsed stem to transform into an expanded stent having a cross-sectional convex shape.

* * * * *